(12) United States Patent
Pei

(10) Patent No.: US 7,538,085 B2
(45) Date of Patent: May 26, 2009

(54) PEPTIDE DEFORMYLASE INHIBITORS AS NOVEL ANTIBIOTICS

(75) Inventor: Dehua Pei, Columbus, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 50 days.

(21) Appl. No.: 11/789,036

(22) Filed: Apr. 23, 2007

(65) Prior Publication Data

US 2007/0259812 A1     Nov. 8, 2007

Related U.S. Application Data

(62) Division of application No. 10/899,207, filed on Jul. 26, 2004, now Pat. No. 7,208,595.

(60) Provisional application No. 60/490,052, filed on Jul. 25, 2003.

(51) Int. Cl.
*A61K 38/12* (2006.01)
*A61K 38/05* (2006.01)
*C07K 5/06* (2006.01)

(52) U.S. Cl. .................... 514/11; 514/2; 514/9; 514/19

(58) Field of Classification Search ................ None
See application file for complete search history.

(56) References Cited

U.S. PATENT DOCUMENTS

| 6,852,752 B2 | 2/2005 | Jacobs et al. |
| 2004/0204378 A1 | 10/2004 | Nelson et al. |
| 2005/0124677 A1 | 6/2005 | Aubart et al. |

OTHER PUBLICATIONS

Chen et al., "Actinonin, a naturally occurring antibacterial agent, is a potent deformylase inhibitor", Biochemistry, 39, pp. 1256-1262, 2000.
Clements, et al., "Antibiotic activity and characterization of BB-3497, a novel peptide deformylase inhibitor", Antimicrobial Agents and Chemotherapy, vol. 45, No. 2, pp. 563-570, Feb. 2001.
Hu, X et al., "Structure-Based Design of a Macrocyclic Inhibitor for Peptide Deformylase", J Med Chem, 46 (18) pp. 3771-3774, 2003.
Apfel et al., Hydroxamic acid derivatives as potent peptide deformylase inhibitors and antibacterial agents, J. Med. Chem., vol. 43 (2000), pp. 2324-2331.
Huntington et al., Synthesis and antibacterial activity of peptide deformylase inihibitors, Biochemistry, vol. 39 (2000), pp. 4543-4551.
Roblin et al., In vitro activity of a new antibiotic, NVP-PDF386 (VRC4887), against Chylamydia pneumoniae, Antimicrob. Agents Chemother., vol. 47 (2003), pp. 1447-1448.
Smith et al., Structure-activity relationship of the peptide deformylase inhibitor BB-3497: modification of the metal binding group, Bioorg. Med. Chem. Lett., vol. 12 (2002), pp. 3595-3599.
Thorarensen et al., Identification of novel potent hydroxamic acid inhibitors of peptidyl deformylase and the importance of the hydroxamic acid functionality on inhibition, Bioorg. Med. Chem. Lett., vol. 11 (2001), pp. 1355-1358.
Wei et al., Identification of a potent peptide deformylase inhibitor from a rationally designed combinatorial library, J. Comb. Chem., vol. 2 (2000), pp. 650-657.

*Primary Examiner*—Andrew D Kosar
(74) *Attorney, Agent, or Firm*—Calfee, Halter & Griswold LLP

(57) ABSTRACT

A macrocyclic peptide deformylase (PDF) inhibitor comprising a peptide or peptide mimetic having three residues, P1', P2', and P3', wherein P2' connects P1' and P3', wherein P1' and P3' each have a side chain, and wherein the side chains on P1' and P3' are crosslinked to form the macrocyclic PDF inhibitor. The side chains of P1' and P3' interact with the PDF active site, and preferably, P2' has a side chain that interacts with a solvent. Also provided are methods of inhibiting the growth of a bacterium, the methods comprising contacting the bacterium with an anti-bacterial effective amount of the inventive macrocyclic PDF inhibitor. Additionally, a method of treating a bacterial infection in a subject comprising administering an effective amount of a macrocyclic PDF inhibitor to a subject in need of treatment. Additionally, methods of preparing macrocyclic PDF inhibitors comprising a) choosing an acyclic base molecule, having at least some PDF inhibitory activity, the acyclic base molecule having a first residue having a first side chain that interacts with the PDF active site and a second residue having a second that interacts with the PDF active site; and b) crosslinking the first side chain and the second side chain to form a macrocyclic PDF inhibitor.

13 Claims, 7 Drawing Sheets

<sup>a</sup>Conditions: (a) pivaloyl chloride, TEA, THF; (b) LiCl, 95% (two steps); (c) TiCl$_4$, DIPEA, CH$_2$Cl$_2$, (HCHO)$_n$, 52%; (d) H$_2$O$_2$, LiOH, THF/H$_2$O; (e) BnONH$_2$, HBTU, TEA, CH$_3$CN, 87% (two steps); (f) DIPAD, Ph$_3$P, THF, 88%; (g) LiOH, i-PrOH/H$_2$O, 93%; (h) HCO$_2$H, Ac$_2$O, CH$_2$Cl$_2$, quantitative.

*Conditions: (a) MsCl, TEA, CH$_2$Cl$_2$; (b) NaN$_3$, DMF-H$_2$O; (c) LiAlH$_4$, Et$_2$O; 57% (3 steps); (d) Boc-*tert*-Leu-OH, EDC, CH$_2$Cl$_2$; (e) TFA, 86% (2 steps); (f) 4, EDC, CH$_2$Cl$_2$, 89%; (g) (Pcy$_3$)$_2$Cl$_2$Ru=CHPh, CH$_2$Cl$_2$, reflux, 83%; (h) Pd/C, H$_2$, MeOH-EtOAc, quantitative.

A

B

PEPTIDE DEFORMYLASE INHIBITORS AS NOVEL ANTIBIOTICS

CROSS-REFERENCE TO RELATED APPLICATIONS

This application is a divisional of Utility patent application Ser. No. 10/899,207, filed Jul. 26, 2004, now U.S. Pat. No. 7,208,595, which claims priority to Provisional Patent Application Ser. No. 60/490,052, filed Jul. 25, 2003, the entirety of which is incorporated herein by reference.

STATEMENT ON FEDERALLY FUNDED RESEARCH

The present invention was made, at least in part, under National Institutes of Health grant AI40575. The government may have certain rights in this invention.

BACKGROUND OF THE INVENTION

The emergence of antibiotic-resistant bacteria has created an urgent demand for new antibacterial agents with novel mechanisms of action. Peptide deformylase (PDF), an essential enzyme involved in bacterial protein biosynthesis and maturation, is one of the few novel targets that are currently being pursued for antibacterial drug design.[1-3] In bacteria, protein synthesis starts with an N-formylmethionine and as a result, all newly synthesized polypeptides carry a formylated N-terminus.[4] PDF catalyzes the subsequent removal of the formyl group from the majority of those polypeptides, many of which undergo further N-terminal processing by methionine aminopeptidase to produce mature proteins. As an essential activity for survival,[5-7] PDF is present in all eubacteria. On the other hand, protein synthesis in the eukaryotic cytoplasm does not involve N-terminal formylation and PDF apparently has no catalytic function in the mammalian mitochondrion.[8]

PDF is a unique metallopeptidase, which utilizes a ferrous ion ($Fe^{2+}$) to catalyze the amide bond hydrolysis.[9,10] Due to sensitivity of the $Fe^{2+}$ center to environmental oxygen and other reactive oxygen species, native PDF is extremely unstable and difficult to work with.[11] However, substitution of $Ni^{2+}$ or $Co^{2+}$ for the $Fe^{2+}$ ion renders the enzyme highly stable while retaining almost full catalytic activity and substrate specificity of the native enzyme. Consequently, most of the recent biochemical, structural, and inhibition studies were carried out with the metal-substituted forms.

Numerous PDF inhibitors have been reported in recent years; essentially all of them are metal chelators. On the basis of the chelator structure, they can be classified into three different types: the thiols,[12-14] the hydroxamates,[15-19] and the N-formylhydroxylamines or reverse hydroxamates.[20,21] Many of the hydroxamate and reverse hydroxamate inhibitors exhibit excellent antibacterial activities in vitro and in animal studies. One of the reverse hydroxamates from British Biotech (BB-86398) is currently in phase I clinical trials. However, since most of these inhibitors still have significant peptide characteristics, there are some concerns about their selectivity (e.g., inhibition of matrix metalloproteases) and in vivo stability (e.g., proteolysis of the peptide bonds).

SUMMARY OF THE INVENTION

Macrocyclic peptide deformylase (PDF) inhibitors are provided. The macrocyclic PDF inhibitor is a peptide or peptide mimetic, comprising in order, residues P1', P2' and P3', wherein P2' connects P1' and P3'. P1' and P3' each have side chains, wherein the side chains on P1' and P3' are crosslinked to form the macrocyclic PDF inhibitors; the crosslinked side chains of P1' and P3' interact with the active site. P2' preferably has a side chain. More preferably, the side chain on P2' interacts with the solvent.

The macrocyclic PDF inhibitors may be depicted by formula I:

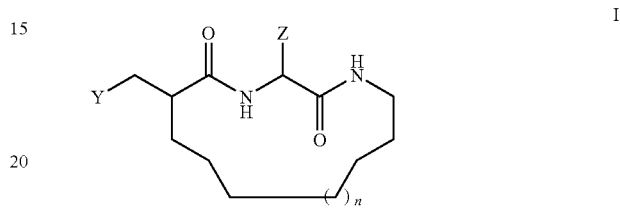

wherein the P2' residue is selected from the group consisting of the 20 naturally occurring L-amino acids, the D-amino acids, amino acid mimetics, and unnatural amino acids wherein Z is selected from the group consisting of H, $C_1$-$C_{10}$ alkyl, $C_1$-$C_{10}$ alkenyl, $C_1$-$C_{10}$ alkynyl; and wherein Z can contain any number of heteroatoms, aromatic rings, or heterocycles; Y is a metal ligand, preferably selected from N-formylhydroxylamine, hydroxamate, sulfhydryl, and carboxyl; more preferably, Y is selected from N-formylhydroxylamine, and hydroxamate; the crosslinked P1' and P3' side chains may comprise saturated hydrocarbons, unsaturated hydrocarbons, wherein the unsaturation may be one or more carbon-carbon double bonds, carbon-carbon triple bonds, or combinations thereof; one or more aryl groups; an arylalkyl; an alkylaryl; a heterocycle; and combinations thereof; and wherein any carbon atom in the cross-linked P1' and P3' side chains may be replaced with a heteroatom selected from the group consisting of O, N, and S; and n is 1 to 13, preferably n is 1 to 8, and more preferably n is 3 to 5.

A preferred subset of macrocyclic PDF inhibitors are those of formula II:

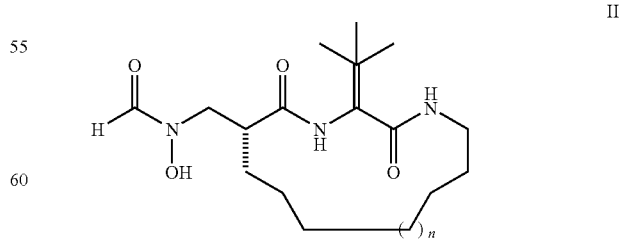

wherein n is 1 to 8, preferably n is 3 to 5.

Another preferred subset of macrocyclic PDF inhibitors are those of formula III:

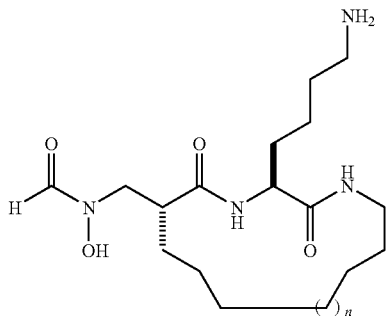

wherein n is 1 to 8, preferably n is 3 to 5.

Another preferred subset of macrocyclic PDF inhibitors are those of formula IV:

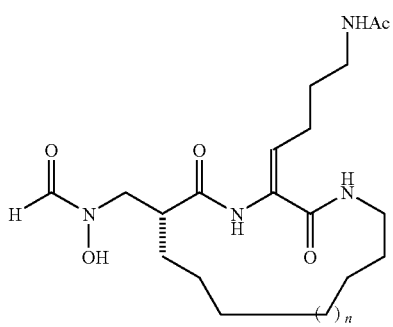

wherein n is 1 to 8, preferably n is 3 to 5.

Also provided are methods of inhibiting the growth of a bacterium, the method comprising contacting the bacterium with an anti-bacterial effective amount of the macrocyclic PDF inhibitor of formula I, II, III, or IV, or a combination thereof.

Also provided are methods of treating a bacterial infection in a subject comprising administering an effective amount of a macrocyclic PDF inhibitor of the present invention to a subject having a bacterial infection. This method of treating a bacterial infection is useful both when the bacterial infection is a drug-sensitive bacterial infection and when the bacterial infection is a drug-resistant bacterial infection. In accordance with the present invention, preferably, the subject is a human subject.

Also provided are methods of preparing a stable, selective PDF inhibitor, the method comprising the steps of a) choosing an acyclic base molecule, preferably a peptide, or peptide mimetic, having at least some PDF inhibitory activity, the acyclic base molecule having a first residue with a first side chain that interacts with the PDF active site and a second residue with a second side chain that interacts with the PDF active site; and b) crosslinking the first side chain and the second side chain to form a macrocyclic PDF inhibitor.

DETAILED DESCRIPTION OF THE INVENTION

Figure 1:
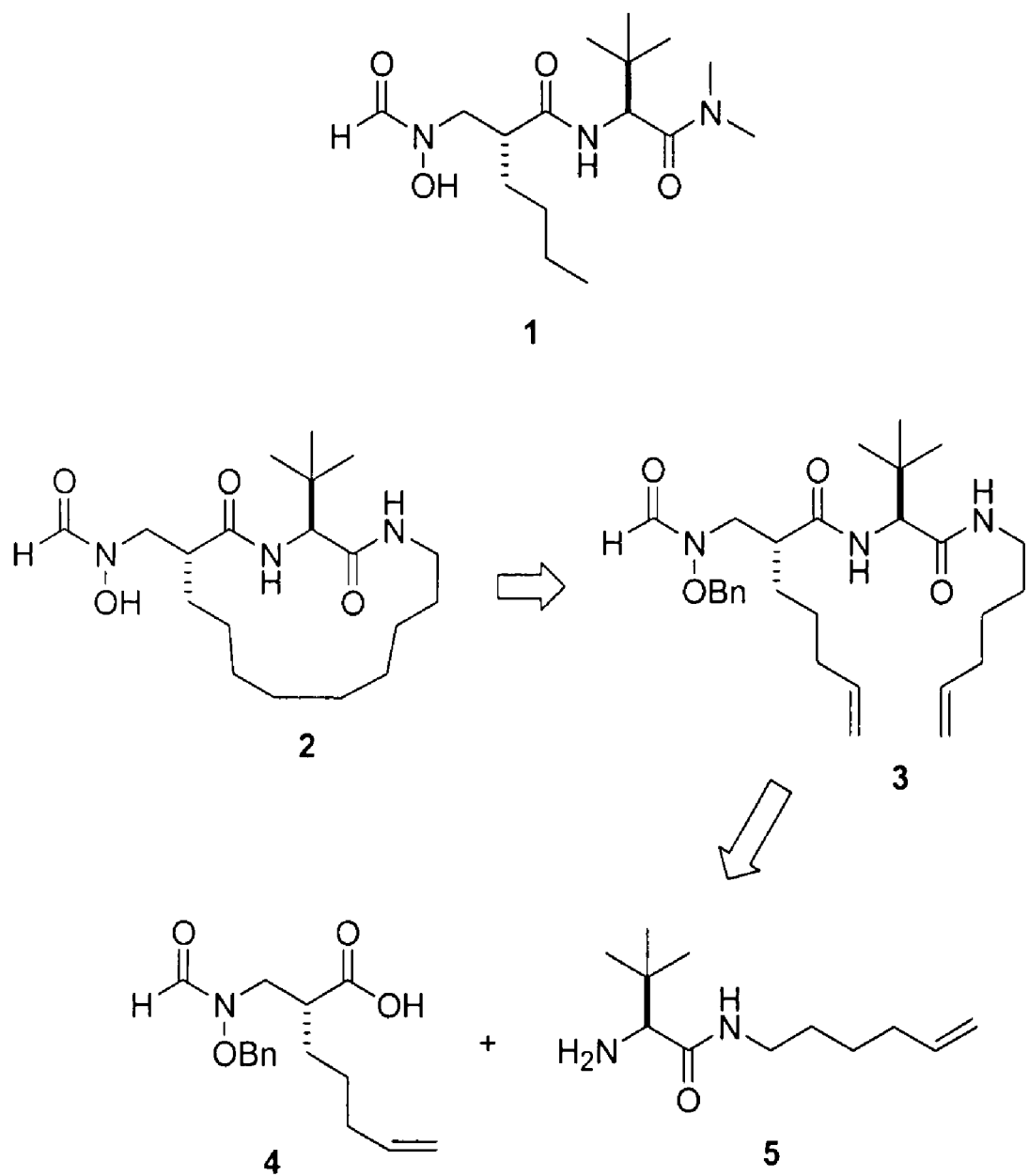
FIG. 1 Retrosynthetic analysis of a macrocyclic peptide deformylase (PDF) inhibitor.

The present invention provides macrocyclic peptide macrocyclic peptide deformylase (PDF) inhibitors, and therapeutic and pharmaceutic compounds comprising the PDF inhibitors. PDF inhibitors are both effective for inhibiting the growth of a broad spectrum of bacteria and are selective to bacteria, they are well-suited for mammalian use, and specifically human use as antibacterial and antibiotic agents. Macrocyclic PDF inhibitors especially useful as antibiotic agents because they are effective against both drug-sensitive and drug-resistant bacteria and they are more stable in physiological conditions than acyclic PDF inhibitors.

The macrocyclic PDF inhibitor is a peptide or peptide mimetic, comprising in order, residues P1', P2' and P3', wherein P2' connects P1' and P3'. P1' and P3' each have side chains, wherein the side chains on P1' and P3' are crosslinked to form the macrocyclic PDF inhibitors; the crosslinked side chains of P1' and P3' interact with the active site. P2' preferably has a side chain. More preferably, the side chain on P2' interacts with the solvent. The macrocyclic PDF inhibitors may be depicted by formula I:

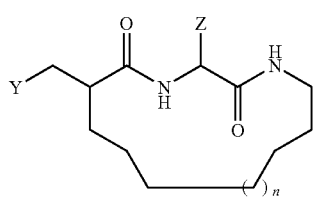

wherein the P2' residue is selected from the group consisting of the 20 naturally occurring L-amino acids, the D-amino acids, amino acid mimetics, and unnatural amino acids; wherein Z is selected from the group consisting of H, $C_1$-$C_{10}$ alkyl, $C_1$-$C_{10}$ alkenyl, $C_1$-$C_{10}$ alkynyl, and wherein Z can contain any number of heteroatoms, aromatic rings, or heterocycles; Y is a metal ligand, preferably selected from N-formylhydroxylamine, hydroxamate, sulfhydryl, and carboxyl, and preferably N-formylhydroxylamide or hydroxamate; the crosslinked P1' and P3' side chains may comprise a saturated hydrocarbon, an unsaturated hydrocarbon wherein the unsaturation may be one or more carbon-carbon double bonds, carbon-carbon triple bonds, or combinations thereof, one or more aryl groups, an arylalkyl, an alkylaryl, a heterocycle, and combinations thereof; and wherein any carbon atom in the cross-linked P1' and P3' side chains may be replaced with a heteroatom selected from the group consisting of O, N, and S; and n is 1 to 13, preferably 1 to 8, and more preferably 3 to 5.

There are several preferred subsets of formula I. One preferred subset of macrocyclic PDF inhibitors are those of formula II:

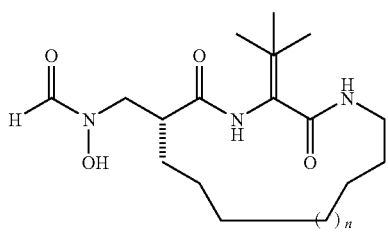

II wherein n is 1 to 8, and is preferably 3 to 5. Another preferred subset of macrocyclic PDF inhibitors are those of formula III:

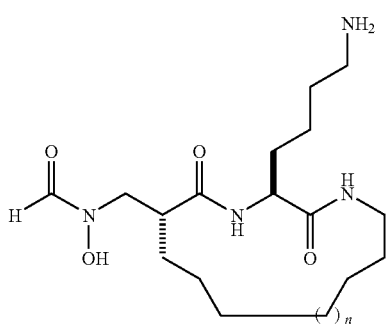

III wherein n is 1 to 8, and preferably 3 to 5. Another preferred subset of macrocyclic PDF inhibitors are those of formula IV:

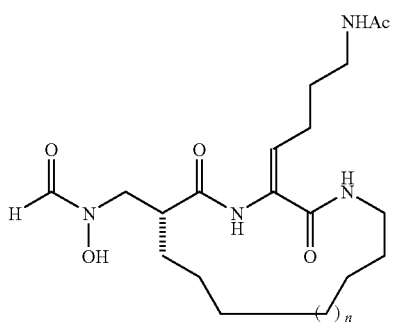

IV wherein n is 1 to 8, and preferably 3 to 5.

Also provided are methods of inhibiting the growth of a bacterium, the method comprising contacting the bacterium with an anti-bacterial effective amount of the macrocyclic PDF inhibitor of formula I, II, III, or IV, or a combination thereof.

The invention further comprises methods of treating a broad spectrum of bacterial infections in a subject comprising administering an effective amount of a macrocyclic PDF inhibitor of the present invention to a subject having a bacterial infection. This method of treating a bacterial infection is useful both when the bacterial infection is a drug-sensitive bacterial infection and when the bacterial infection is a drug-resistant bacterial infection. In accordance with the present invention, preferably, the subject is a human subject.

Also provided are methods of preparing a stable, selective PDF inhibitor, the method comprising the steps of a) choosing an acyclic base molecule, having at least some PDF inhibitory activity, the acyclic base molecule being a peptide or peptide mimetic, the acyclic base molecule having a first residue having a side chain that interacts with the PDF active site and a third residue having a side chain that interacts with the PDF active site; and b) crosslinking the side chains on the first residue and the second residue to form a macrocyclic PDF inhibitor.

The present invention comprises macrocyclic PDF inhibitors, which are useful broad spectrum antibacterial agents, and particularly useful as broad spectrum antibiotics. The invention further comprises a pharmaceutical composition comprising a therapeutically effective amount of a macrocyclic PDF inhibitor, or a derivative or pharmaceutically acceptable salt thereof, in association with at least one pharmaceutically acceptable carrier, adjuvant, or diluent (collectively referred to herein as "carrier materials") and, if desired, other active ingredients. The active compounds of the present invention may be administered by any suitable route known to those skilled in the art, preferably in the form of a pharmaceutical composition adapted to such a route, and in a dose effective for the treatment intended. The active compounds and composition may, for example, be administered orally, intra-vascularly, intraperitoneally, intranasal, intrabronchial, subcutaneously, intramuscularly or topically (including aerosol). With some subjects local administration, rather than system administration, may be preferred.

The terms "therapeutically effective" and "pharmacologically effective" are intended to qualify the amount of macrocyclic PDF inhibitor is necessary to inhibit growth of bacteria. A therapeutically effective or pharmacologically effective amount will depend on the particular macrocyclic inhibitor, the bacterium, as well as other factors. A therapeutically effective or pharmacologically effective amount can readily be determined by those skilled in the art.

The compounds of the present invention can be formulated into suitable pharmaceutical preparations such as tablets, capsules, or elixirs for oral administration or in sterile solutions or suspensions for parenteral administration. The therapeutic agents described herein can be formulated into pharmaceutical compositions using techniques and procedures well known in the art.

About 0.1 to 1000 mg of a macrocyclic PDF inhibitor described herein is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions can be formulated in a unit dosage form, each dosage containing from about 1 to about 500 mg, or about 10 to about 100 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

To prepare compositions, one or more of the therapeutic agents employed in the methods of the invention are mixed with a suitable pharmaceutically acceptable carrier. Upon mixing or addition of the therapeutic agent(s), the resulting mixture may be a solution, suspension, emulsion, or the like. These may be prepared according to methods known to those skilled in the art. The form of the resulting mixture depends upon a number of factors, including the intended mode of administration and the solubility of the compound in the selected carrier or vehicle. The effective concentration is sufficient for treating a bacterial infection and may be empirically determined.

Pharmaceutical carriers or vehicles suitable for administration of the present therapeutic agents include any such carriers suitable for the particular mode of administration. In addition, the active materials can also be mixed with other active materials that do not impair the desired action, or with materials that supplement the desired action, or have another action. The present therapeutic agents may be formulated as the sole pharmaceutically active ingredient in the composition or may be combined with other active ingredients. Derivatives of the present therapeutic agents, such as salts or prodrugs, may also be used in formulating effective pharmaceutical compositions.

The present therapeutic agents may be prepared with carriers that protect them against rapid elimination from the body, such as time-release formulations or coatings. Such carriers include controlled release formulations, such as, but not limited to, microencapsulated delivery systems. The active compound can be included in the pharmaceutically acceptable carrier in an amount sufficient to exert a therapeutically useful effect in the absence of undesirable side effects on the patient treated.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, or fruit flavoring.

The term "subject" for purposes of treatment includes any human or animal subject in need of antibacterial or antibiotic treatment. Besides being useful for human treatment, the compounds of the present invention are also useful for veterinary treatment of mammals, including companion animals and farm animals, such as, but not limited to dogs, cats, horses, cows, sheep, and pigs. Preferably, subject means a human.

Where the term alkyl is used, either alone or with other terms, such as haloalkyl or alkylaryl, it includes $C_1$ to $C_{10}$ linear or branched alkyl radicals, examples include methyl, ethyl, propyl, isopropyl, butyl, tert-butyl, and so forth. The term "haloalkyl" includes $C_1$ to $C_{10}$ linear or branched alkyl radicals substituted with one or more halo radicals. The term "halo" includes radicals selected from F, Cl, Br, and I.

The term aryl, used alone or in combination with other terms such as alkylaryl, haloaryl, or haloalkylaryl, includes such aromatic radicals as phenyl, biphenyl, and benzyl, as well as fused aryl radicals such as naphthyl, anthryl, phenanthrenyl, fluorenyl, and indenyl and so forth. The term "aryl" also encompasses "heteroaryls," which are aryls that have carbon and one or more heteroatoms, such as O, N, or S in the aromatic ring. Examples of heteroaryls include indolyl, pyrrolyl, and so on. "Alkylaryl" or "arylalkyl" refers to alkyl-substituted aryl groups such as butylphenyl, propylphenyl, ethylphenyl, methylphenyl, 3,5-dimethylphenyl, tert-butylphenyl and so forth. "Haloaryl" refers to aryl radicals in which one or more substitutable positions has been substituted with a halo radical, examples include fluorophenyl, 4-chlorophenyl, 2,5-chlorophenyl and so forth. "Haloalkylaryl" refers to aryl radicals that have a haloalkyl substituent. Examples of haloalkylaryls include such radicals as bromomethylphenyl, 4-bromobutylphenyl and so on. Carboxyamide refers to the group $CONH_2$, and sulfonamide refers to the group $SO_2NH_2$.

Also included in the family macrocyclic PDF inhibitors are the pharmaceutically acceptable salts thereof. The phrase "pharmaceutically acceptable salts" connotes salts commonly used to form alkali metal salts and to form addition salts of free acids or free bases. The nature of the salt is not critical, provided that it is pharmaceutically acceptable. Suitable pharmaceutically acceptable acid addition salts of the macrocyclic PDF inhibitors may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, ambonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, galactaric, and galacturonic acids. Suitable pharmaceutically acceptable base addition salts of macrocyclic PDF inhibitors include metallic salts made from aluminum, calcium, lithium, magnesium, potassium, sodium, and zinc. Alternatively, organic salts made from N,N'-dibenzylethylenediamine, chloroprocaine, choline, diethanolamine, ethylenediamine, meglumine (N-methylglucamine) and procaine may be used form base addition salts of the macrocyclic PDF inhibitors. All of these salts may be prepared by conventional means from the corresponding macrocyclic PDF inhibitors by reacting, for example, the appropriate acid or base with the macrocyclic PDF inhibitor.

Derivatives are intended to encompass any compounds which are structurally related to the macrocyclic PDF inhibitors or which possess the substantially equivalent activity, as measured by the derivative's ability to selectively inhibit growth of bacteria. By way of example, such compounds may include, but are not limited to, prodrugs thereof. Such compounds can be formed in vivo, Such as by metabolic mechanisms.

Structural studies of several PDF-inhibitor complexes[20,24,25] have revealed that the inhibitors are bound in an extended conformation and the P1' and P3' side chains are similarly oriented. While the P2' side chain is extended toward solvent, the P1' and P3' side chains are engaged in intimate interactions with the enzyme. The P1' side chain (usually an n-butyl group) fits into a deep hydrophobic pocket in the PDF active site. The P3' side chain makes hydrophobic contacts with a shallow pocket near the active site as well as one face of the P1' side chain. It appears that covalent crosslinking of the P1' and P3' side chains would be accommodated by the PDF active site. Moreover, the rigidity introduced by cyclization may lock the inhibitor into the PDF-binding conformation and thus improve binding affinity as well as selectivity by preventing binding to other enzymes.

Molecular modeling indicated that the nonyl group should have the sufficient length to link the P1' Cα carbon and the P3' amino group, while maintaining the extended conformation of the peptide backbone. Retrosynthetic analysis (Scheme 1) shows that the macrocycle can be conveniently prepared via olefin metathesis from diene 3, which in turn can be prepared from acid 4 and amine 5. This synthetic strategy would allow for the convergent synthesis of macrocycles of different ring sizes by using the common acid 4 and varying the length of the alkenylamino group in 5.

Synthesis of acid 4 started from the commercially available 6-heptenoic acid (Scheme 2). A hydroxymethyl group was introduced at the C-2 position using 4S-benzyloxazolidin-2-one as the chiral auxiliary group.[26] Removal of the auxiliary group by hydrolysis followed by condensation with O-benzylhydroxylamine gave the hydroxamate 9, which was converted into β-lactam 10 through an intramolecular Mitsunobu reaction.[27] Hydrolysis of the β-lactam furnished acid 11, which was subsequently formylated at its benzyloxyamine moiety to give the acid 4.

Synthesis of compound 2 is shown in Scheme 3. Amine 13, which was obtained from the corresponding alcohol 12, was condensed with N-Boc-tert-leucine. Treatment of the resulting amide with TFA resulted in the amine 5. Coupling of amine 5 with acid 4 gave the diene 3. The terminal alkenes were crosslinked using Grubbs' ruthenium catalyst[28,29] to produce the 15-membered macrocycle 14. The configuration of the ring C=C bond in this intermediate was not determined. Catalytic hydrogenation of 14 reduced the double bond and simultaneously removed the benzyl group from the N-hydroxyl moiety to give the N-formylhydroxylamine 2. NMR and HPLC analyses indicated a purity of ~96%.

Compound 2 was assayed against Co(II)-substituted E. coli PDF using a dehydrogenase assay.[30,31] It acted as a potent inhibitor, with an apparent $K_I$ value of 0.67±0.2 nM. Thus, cyclization of the P1' and P3' side chains renders compound 2 ~10-fold more potent than the acyclic parent compound 1 ($IC_{50}$=7 nM).[20] To gain insight into the mechanism of inhibition, the Co-PDF-inhibitor 2 complex was examined by UV-visible spectroscopy. Binding of the inhibitor resulted in marked blue shift (by ~40 nm) and reduction in the maximum intensity of the D-D transition bands in the absorption spectrum of the cobalt ion (FIG. 1a). This result suggests that compound 2 is directly ligated to the metal ion. The maximum absorptivity of ~200 $M^{-1}$ $cm^{-1}$ for the PDF-inhibitor complex is consistent with a bidentate interaction between the N-formylhydroxylamine group and the metal and the formation of a penta-coordinated cobalt.[32] Molecular modeling showed that inhibitor 2 fits snugly in the active site of E. coli PDF (FIG. 1b). The N-formylhydroxylamine is coordinated with the metal ion via both oxygen atoms. There are three hydrogen bonds formed between the protein and the inhibitor: from Ile-44 backbone amide to P1' carbonyl, from P2' amide to Gly-89 carbonyl, and from Gly-89 amide to P2' carbonyl group. The nonyl group is engaged in extensive hydrophobic interactions with protein side chains including those of Ile-44, Ile-86, Glu-88, Ile-128, Cys-129, and His-132. Overall, these interactions are very similar to those observed in the PDF-inhibitor 1 complex.[20]

The in vitro antibacterial activity of the cyclic inhibitor was tested against E. coli and Bacillus subtilis, the representative Gram-negative and Gram-positive bacteria, respectively.

Figure 2:
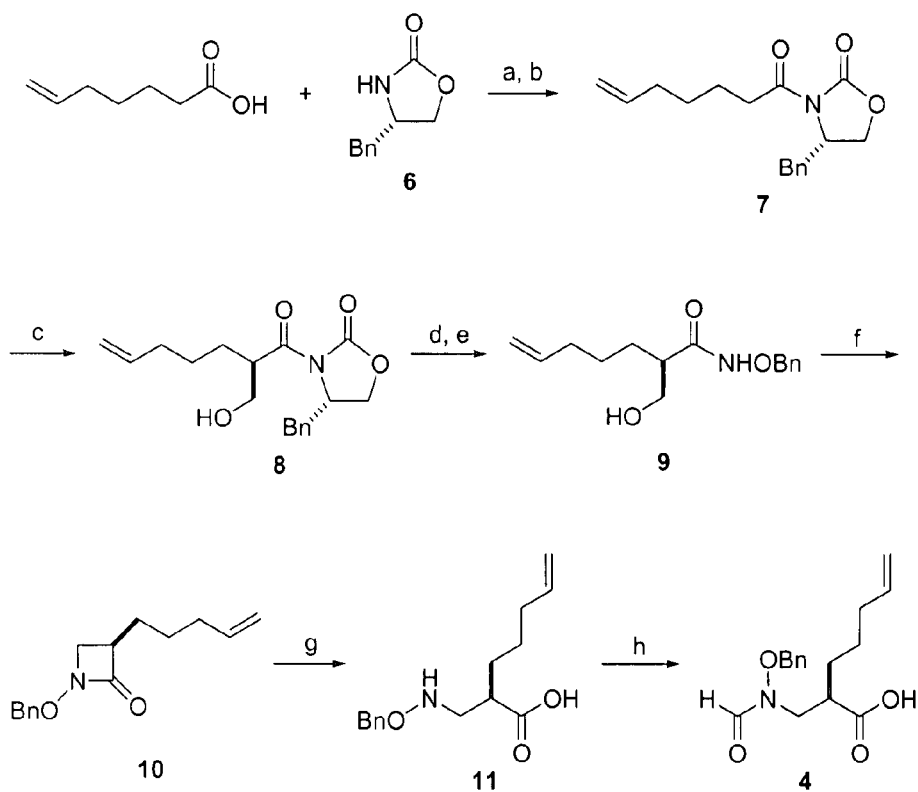
FIG. 2 Synthetic scheme for acid 4.
Figure 3:
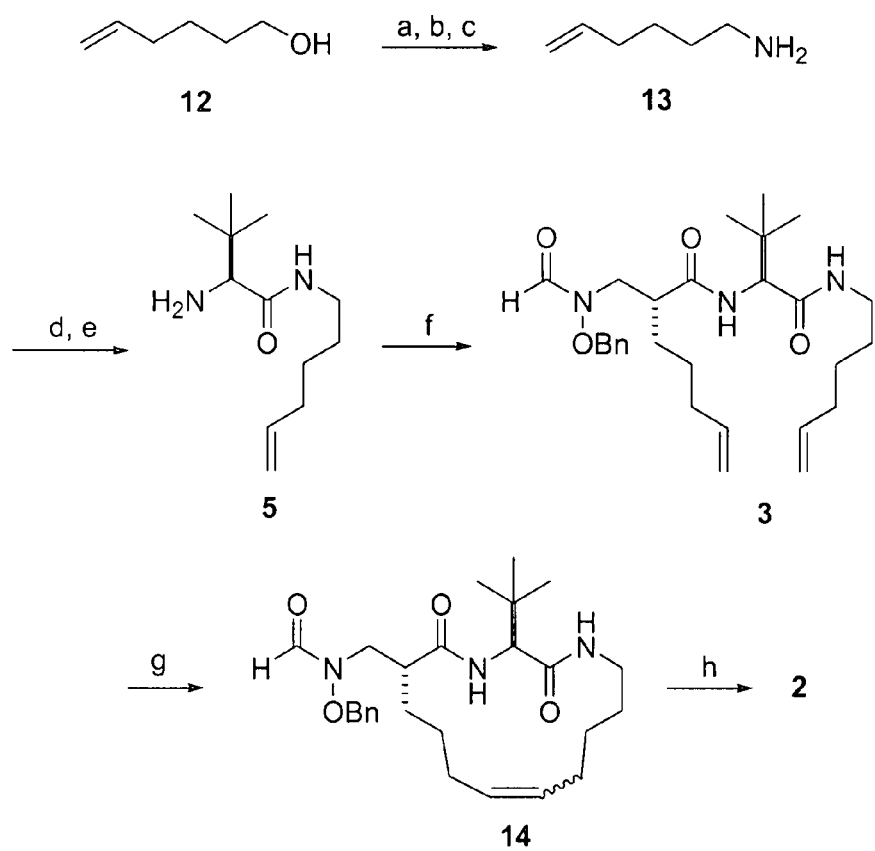
FIG. 3 Synthetic scheme for compound 2.
Figure 4:
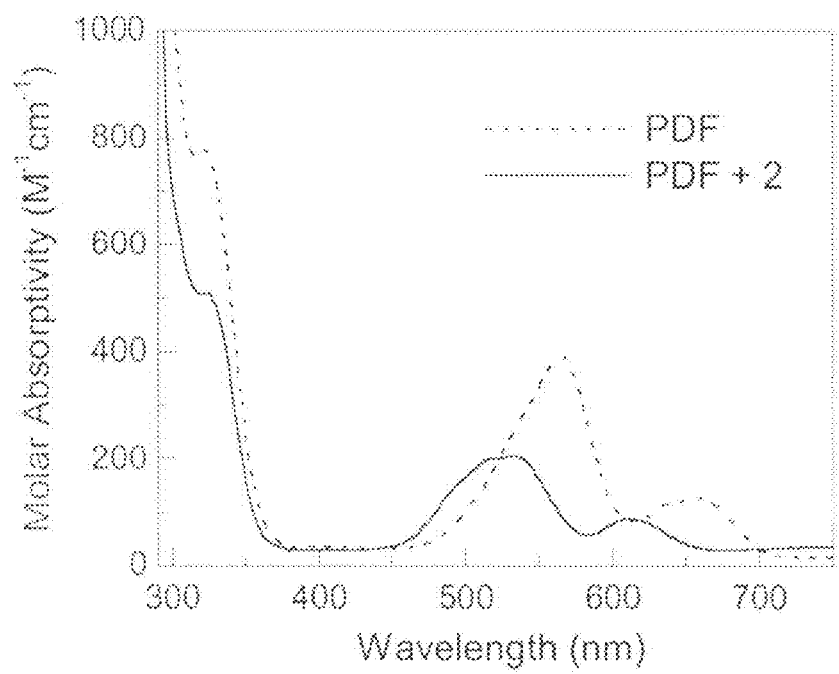
FIG. 4 (A) Electronic absorption spectra of Co(II)-substituted PDF (240 µM) in the absence and presence of inhibitor 2 (500 µM). (B) Model showing the binding mode of inhibitor 2 to the $E.\ coli$ PDF active site. Modeling was carried out by docking compound 2 into the structure of $E.\ coli$ PDF bound with reverse hydroxamate inhibitor 1 (PDB access code 1G27). Protein residues involved in hydrophobic interactions with the inhibitor nonyl ring, as well as the metal ligands are labeled.
Figure 4:
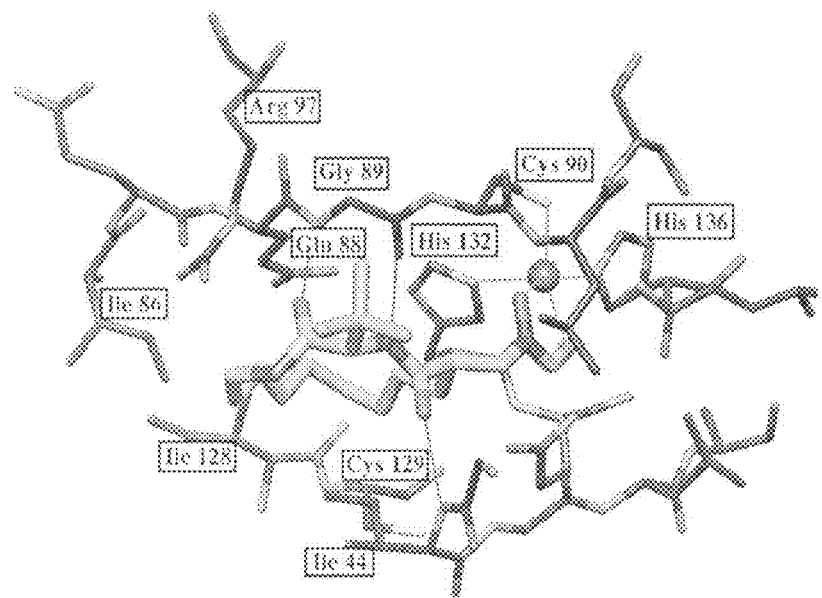
Figure 5:
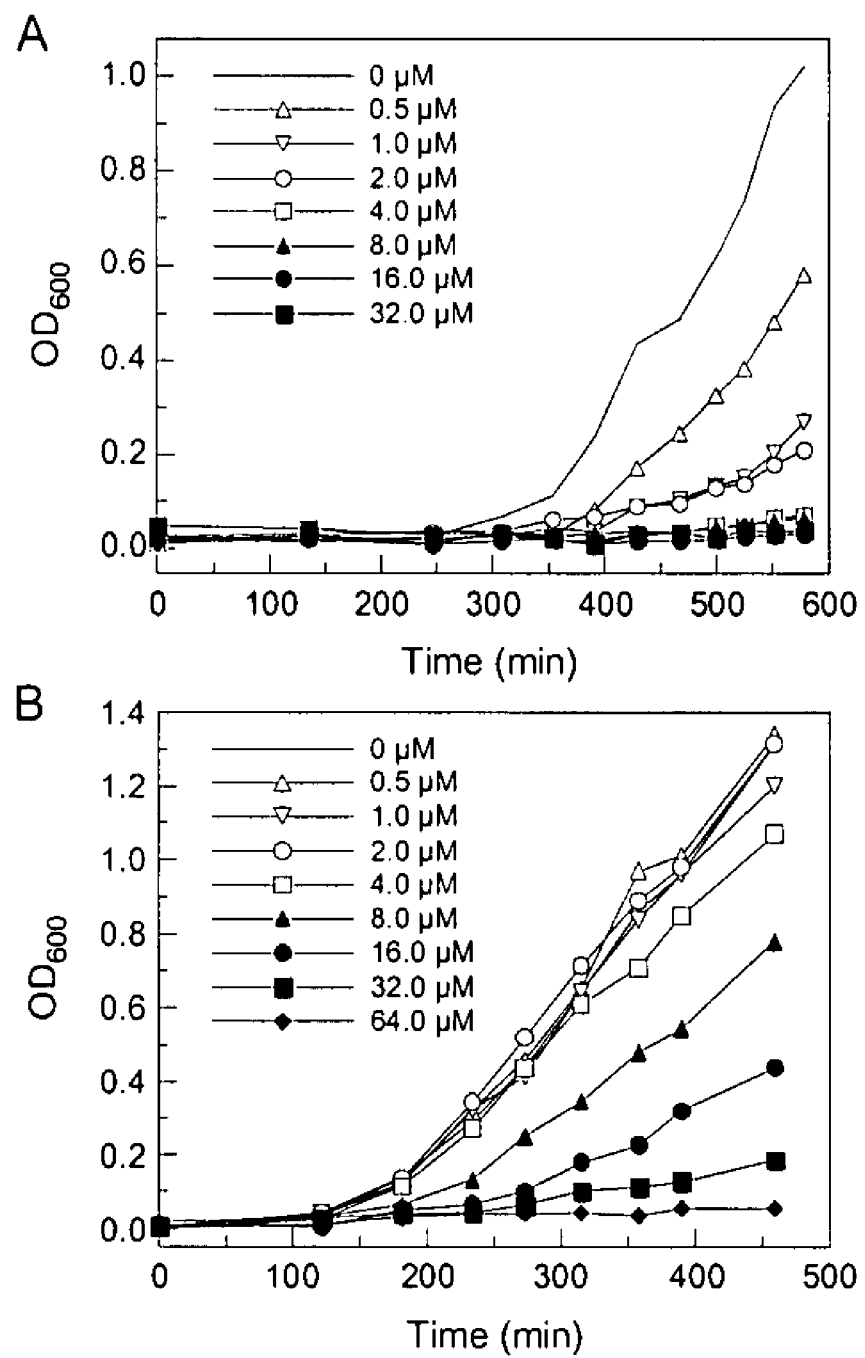
FIG. 5 Inhibition of $B.\ subtilis$ (A) and $E.\ coli$ (B) cell growth by inhibitor 2. An overnight culture was diluted 1000-fold into 2 mL of fresh LB medium containing the specified concentrations of inhibitor 2 and incubated at 37° C. Cell densities were measured at the specified times on a UV-vis spectrophotometer.
Figure 6:
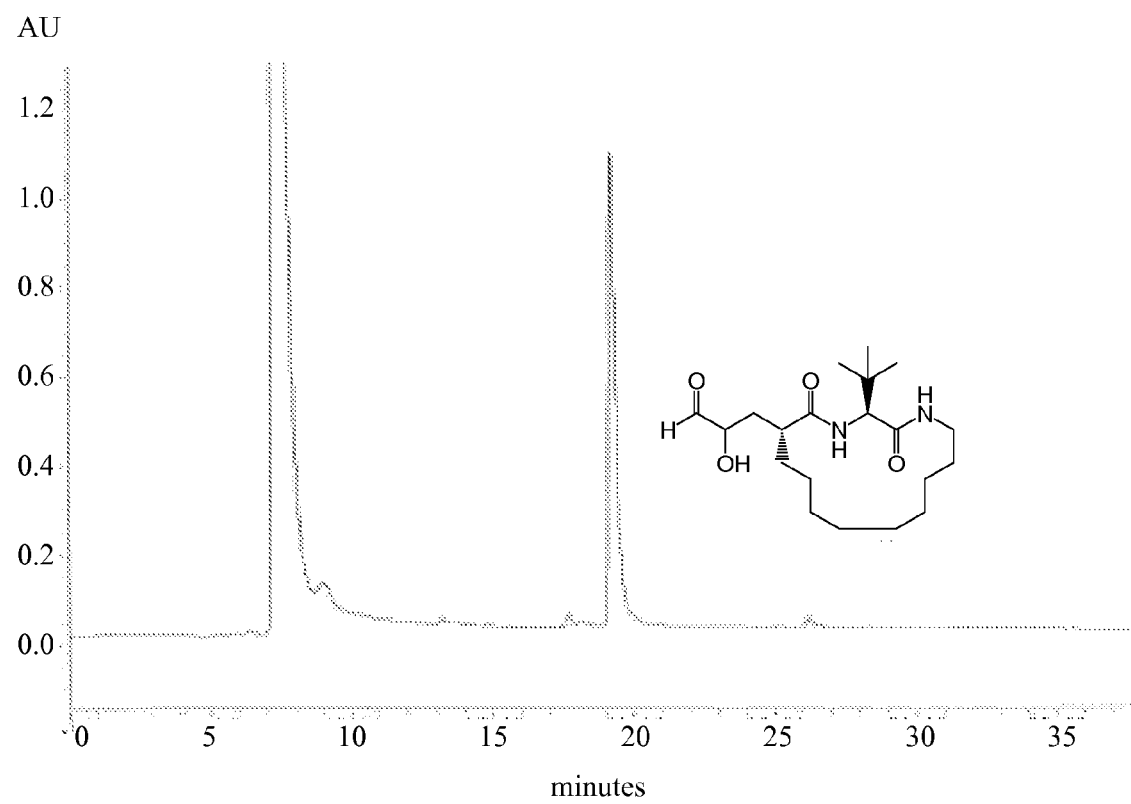
FIG. 6 HPLC tracing for compound 2 (monitored at 214 nm). The peak at $t_R$=~8 min. is DMSO.

FIG. 2 shows the bacterial cell growth curves in the presence of varying concentrations of inhibitor 2. Compound 2 exhibited potent antibacterial activity against B. subtilis, with a minimal inhibitory concentration (MIC) of 2-4 μM (or 0.7-1.4 μg/mL). It is only moderately active against E. coli, with an MIC of ~32 μM (~12 μg/mL). The lower activity against E. coli is likely due to its inefficient permeation of the bacterial outer membrane and/or being removed from the cells by the efflux pump.

In conclusion, based on our earlier observations that the P1' and P3' side chains of PDF inhibitors are closely packed in the PDF-inhibitor complex, we have developed a new class of macrocyclic PDF inhibitor by covalently linking the two side chains. The cyclic inhibitor is highly potent against PDF and has excellent to moderate antibacterial activity against both Gram-positive and Gram-negative bacteria. This result demonstrates that cyclization of the P1' and P3' side chains is a viable approach to developing potent PDF inhibitors. Due to their more rigid structures, cyclic inhibitors of this type may also have improved stability and selectivity.

Based on earlier observations that the $P_1$' and $P_3$' side chains of PDF inhibitors are closely packed in the PDF-inhibitor complex, a new class of macrocyclic PDF inhibitors has been developed by covalently linking the two side chains. The ring size greatly affects the inhibitor properties, with 15-17-membered rings as the optimal ring size. Compared to their acyclic counterparts, the cyclic inhibitors of the optimal ring sizes show much higher potency against PDF (>20-fold), improved stability against proteolytic degradation, and higher selectivity for PDF over other metalloproteases. To the best of our knowledge, the cyclic inhibitors rank among the most potent inhibitors reported to date against the PDF enzyme. Furthermore, the inventive inhibitors have good antibacterial activity against a wide spectrum of pathogens.

Experimental Methods

General. Cobalt(II)-substituted Escherichia coli PDF was overexpressed and purified to apparent homogeneity as previously described.[33] Formate dehydrogenase was purchased from Sigma (St. Louis, Mo.). Aeromonas aminopeptidase was purified according to literature procedure.[34] All chemicals were purchased from either Sigma-Aldrich (St. Louis, Mo.) or Advanced ChemTech (Louisville, Ky.). High-resolution mass spectrometry was performed on a 3T FT-ICR mass spectrometer equipped with an electrospray ionization source. Absorption spectroscopic measurements were performed on a Perkin-Elmer Lambda 20 UV/Vis spectrophotometer.

Synthesis of Macrocycle (2)

4S-Benzyl-3-(6-heptenoyl)-oxazolidin-2-one (7). To the solution of 6-heptenoic acid (5.00 mL, 36.9 mmol) and triethylamine (12.2 mL, 92.3 mmol) in THF (200 mL) was added dropwise pivaloyl chloride (4.43 mL, 36.0 mmol) at −10° C. After addition the mixture was stirred for another hour. Lithium chloride (1.53 g, 36 mmol) and 2-oxazolidinone 6 (6.20 g, 35 mmol) were added. After the reaction was complete (~6 h), the solvent was evaporated and the residue was partitioned between ethyl acetate (150 mL) and a 5% sodium bicarbonate solution (50 mL). The organic layer washed with 5% $NaHCO_3$ (2×40 mL) and brine (40 mL) and dried over sodium sulfate. Flash chromatography using ethyl acetate and hexane as eluent gave 9.55 g of a colorless viscous liquid (yield 95%). $^1$H NMR (400 MHz, $CDCl_3$) δ 7.33-7.19 (m, 5H), 5.81 (m, 1H), 5.00 (m, 2H), 4.67 (m, 1H), 4.15 (m, 2H), 3.26 (dd, J=3.3, 13.3 Hz, 1H), 2.93 (m, 2H), 2.76 (dd, J=9.5, 13.3 Hz, 1H), 2.10 (m, 2H), 1.71 (m, 2H), 1.47 (m, 2H); $^{13}$C NMR (100 MHz, $CDCl_3$) δ 173.2, 153.4, 138.4, 135.4, 129.4, 128.9, 127.3, 114.7, 66.2, 55.1, 37.9, 35.3, 33.5, 28.3, 23.7. HRESI-MS: $C_{17}H_{21}NO_3Na^+$ ([M+Na]$^+$), calc'd 310.1414, found 310.1421.

4S-Benzyl-3R-(2-hydroxymethyl-6-heptenoyl)-oxazolidin-2-one (8). To the solution of 4S-benzyl-3-(6-heptenoyl)-oxazolidin-2-one 7 (2.25 g, 7.8 mmol) in dichloromethane (100 mL) was added titanium chloride (1.0 M in dichloromethane, 8.2 mmol). The resulting solution was stirred for 10 min at 0° C. Then diisopropylethylamine (1.50 mL, 8.6 mmol) was added to the resulting yellow slurry, and the solution turned reddish brown. After the mixture was stirred for 30 min., parafomaldehyde (0.35 g, 11.7 mmol) was added, followed by the addition of a second batch of titanium chloride (8.2 mmol). The reaction was quenched after 2 h by the addition of a saturated ammonium chloride solution (100 mL). The organic layer was separated and the aqueous layer was extracted with dichloromethane (2×40 mL). The combined organic phase washed with brine (2×40 mL) and dried over sodium sulfate. The crude product was purified by flash chromatography using ethyl acetate and hexane as the eluent to afford 1.30 g of the desired product (52% yield). $^1$H NMR (250 MHz, $CDCl_3$) δ 7.34-7.20 (m, 5H), 5.79 (m, 1H), 4.96 (m, 2H), 4.70 (m, 1H), 4.19 (m, 2H), 3.95 (m, 1H), 3.88 (m, 2H), 3.28 (dd, J=3.4, 13.5 Hz, 1H), 2.81 (dd, J=9.3, 13.5 Hz, 1H), 2.23 (brs, 1H), 2.05 (m, 2H), 1.71-1.40 (m, 4H); $^{13}$C NMR (63 MHz, $CDCl_3$) δ 176.2, 154.0, 138.6, 135.6, 129.9, 129.4, 127.8, 115.3, 66.6, 64.3, 55.9, 45.9, 38.3, 34.1, 28.4, 26.9. HRESI-MS: $C_{18}H_{23}NO_4Na^+$ ([M+Na]$^+$), calcd 340.1519, found 340.1527.

N-Benzyloxy-2R-hydroxymethyl-6-heptenamide (9). To a solution of compound 8 (0.51 g, 1.6 mmol) in THF-$H_2O$ (24 mL, 5:1) was added hydrogen peroxide (30% concentration, 6.4 mmol) and then lithium chloride hydrate (0.13 g, 3.2 mmol) at 0° C. After the reaction was complete (~2 h), sodium sulfite (1.23 g, 3.2 mmol) was added and the solution was stirred for 10 min. THF was removed under vacuum and the remaining aqueous solution washed with dichloromethane (3×40 mL). After acidification with 1 N HCl to pH~3, the solution was extracted with ethyl acetate (3×40 mL). The organic layers were combined, dried over sodium sulfate, and concentrated to give 2R-hydroxymethyl-6-heptenoic acid (0.27 g). $^1$H NMR (250 MHz, $D_2O$) δ 6.03 (m, 1H), 5.16 (m, 2H), 3.88 (d, J=6.0 Hz, 2H), 2.78 (m, 1H), 2.23 (m, 2H), 1.76-1.53 (m, 4H); $^{13}$C NMR (63 MHz, $D_2O$) 179.8, 139.6, 115.0, 62.9, 48.3, 33.2, 27.7, 26.1. The above crude acid, O-benzylhydroxylamine (0.31 g, 2.5 mmol), and triethylamine (0.28 mL, 2.0 mmol) were dissolved in acetonitrile (8 mL), to which 2-(1H-benzotriazol-1-yl)-N,N,N',N'-tetramethyluronium hexafluorophosphate (HBTU) (1.10 g, 1.7 mmol) was added at 0° C. After stirring for 3 h, the solution was diluted with ethyl acetate (100 mL), and washed with 1 N HCl (2×40 mL), 10% sodium bicarbonate (2×40 mL), and brine (40 mL). The solution was dried over sodium sulfate and evaporated to give the crude product, which was purified by silica gel chromatography (87% yield). $^1$H NMR (250 MHz, $CDCl_3$-$CD_3COCD_3$) δ 9.80 (brs, 1H), 7.37 (m, 5H), 5.78 (m, 1H), 4.97 (m, 4H), 3.66 (m, 2H), 2.25 (brs, 1H), 2.12 (m, 2H), 1.78 (m, 1H), 1.45 (m, 3H).

N-Benzyloxy-α-(4-penten-1-yl)-β-Lactam (10). Compound 9 (1.74 g, 6.6 mmol) and triphenylphosphine (4.00 g, 15.3 mmol) were dissolved in THF (150 mL) and diisopropyl azodicarboxylate (2.70 mL, 13.7 mmol) was added. The yellow solution was stirred overnight at room temperature. After removing the solvent, the crude product was purified by flash chromatography on a silica gel column (1.42 g, 88% yield). $^1$H NMR (250 MHz, $CDCl_3$): δ 7.37 (m, 5H), 5.76 (m, 1H), 5.01 (m, 2H), 4.93 (s, 2H), 3.35 (dd, J=5.0, 4.7 Hz, 1H), 2.90 (dd, J=2.3, 4.4 Hz, 1H), 2.88 (m, 1H), 2.03 (m, 2H), 1.74 (m, 1H), 1.58-1.25 (m, 3H). $^{13}$C NMR (63 MHz, $CDCl_3$) δ 167.2, 138.4, 135.7, 129.6, 129.3, 129.0, 115.4, 78.0, 51.8, 45.4, 33.7, 28.4, 26.7.

2R-[(Benzyloxyamino)methyl]-6-heptenoic acid (11). To a solution of β-lactam 10 (1.00 g, 4.1 mmol) in isopropanol (15 mL) was added lithium hydroxide hydrate (0.21 g, 4.9 mmol) in water (7 mL). The mixture was stirred overnight and then washed with dichloromethane (2×15 mL). The aqueous solution was acidified with 1 N HCl to pH 2-3 and extracted with ethyl acetate (3×40 mL). The combined organic layers were washed with brine (20 mL), dried over sodium sulfate, and concentrated to afford the β-amino acid (0.92 g, 93% yield). $^1$H NMR (250 MHz, $CDCl_3$): δ 8.36 (brs, 2H), 7.32 (m, 5H), 5.78 (m, 1H), 4.98 (m, 2H), 4.74 (s, 2H), 3.17 (m, 2H), 2.76 (m, 1H), 2.07 (m, 2H), 1.58-1.23 (m, 4H).

2R-[(N-Benzyloxy-N-formylamino)methyl]-6-heptenoic acid (4). To a solution of acid 11 (1.32 g, 5.0 mmol) in dichloromethane (20 mL) was added formic acid (20.0 mmol) and acetic anhydride (10.0 mmol) in an ice-water bath. The mixture was allowed to warm to room temperature and stirred overnight. The volatile material was removed under vacuum to give formylated amino acid 4 in quantitative yield. $^1$H NMR (400 MHz, $CD_3OD$) δ 8.08 (brs, 0.5H), 7.94 (brs, 0.5H), 7.35 (m, 5H), 5.74 (m, 1H), 4.98-4.87 (m, 2H), 3.78 (m, 1.5H), 3.42 (m, 0.5H), 2.71 (m, 1H), 2.02 (m, 2H), 1.55-1.34 (m, 4H); $^{13}$C NMR (63 MHz, $CD_3OD$) δ165.2, 161.1, 139.7, 131.4, 131.2, 130.5, 130.1, 115.8, 78.7, 46.6, 44.9, 34.9, 30.6, 27.7. HRESI-MS: $C_{16}H_{21}NO_4Na^+$ ([M+Na]$^+$), calc'd 314.1363, found 314.1375.

5-Hexen-1-ylamine (13). To a solution of 5-hexen-1-ol (5.0 mmol) and triethylamine (5.5 mmol) in dichloromethane (20 mL) was added methanesulfonyl chloride (5.5 mmol) dropwise at −5° C. The mixture was continuously stirred until the reaction was complete (~2 h). Dichloromethane (50 mL) was added to the mixture followed by washing with 10% sodium bicarbonate solution (2×15 mL) and brine (15 mL). The organic layer was dried over sodium sulfate and concentrated to give 5-hexenyl methanesulfonate, which was used next without further purification. The methanesulfonyl ester (4.0 mmol) and sodium azide (10 mmol) were dissolved in 8:1 DMF-$H_2O$ (16 mL) and stirred overnight at 50° C. The mixture was allowed to cool to room temperature, diluted in 50 mL of water, and extracted with diethyl ether (3×30 mL). The ethereal layers were combined, washed with brine (2×15 mL), dried over sodium sulfate, and concentrated in vacuo to give 5-hexenyl azide. The azide (5.0 mmol) was dissolved in diethyl ether (50 mL) and lithium aluminum hydride (5.0 mmol) was added in three portions under argon in a water bath. The grayish suspension was vigorously stirred for ~40 min and then quenched by the addition of water (5 mL). Sodium hydroxide solution was added to dissolve the solid and the resulting solution was extracted with diethyl ether (5×30 mL). The organic phase was dried over sodium sulfate and concentrated to give amine 13 (57% yield from the alcohol). $^1$H NMR (250 MHz, $D_2O$): δ 6.11-5.95 (m, 1H), 5.26-5.14 (m, 2H), 3.14 (t, J=7.3 Hz, 2H), 2.25 (m, 2H), 1.87-1.75 (m, 2H), 1.67-1.58 (m, 2H).

N-(5-Hexen-1-yl)-L-tert-leucinamide (5). L-Boc-tert-leucine (0.26 g, 1.1 mmol) and amine 13 (as its trifluoroacetate salt, 0.24 g, 1.1 mmol) were dissolved in a solution of dichloromethane (10 ml) and triethylamine (0.16 mL, 1.2 mmol), and then 1-(3-dimethylaminopropyl)-3-ethylcarbodiimide hydrochloride (EDC) (0.21 g, 1.1 mmol) was added. After stirring for about 2 h the mixture was diluted with ethyl acetate (60 mL), washed with 5% $NaHCO_3$ (2×40 mL) and brine, dried over sodium sulfate, filtered and concentrated to dryness. The residue was purified by flash chromatography to give the amide (0.30 g, 88%). $^1$H NMR (250 MHz, $CDCl_3$) δ 6.73 (m, 1H), 5.77 (m, 1H), 5.48 (d, J=9.5 Hz, 1H), 4.95 (m, 2H), 3.92 (d, J=9.5 Hz, 1H), 3.31 (m, 1H), 3.12 (m, 1H), 2.04 (m, 2H), 1.57-1.35 (m, 4H), 1.43 (s, 9H), 1.00 (s, 9H); $^{13}$C NMR (63 MHz, $CDCl_3$) δ 171.3, 156.4, 138.7, 115.1, 79.7, 62.6, 39.6, 34.7, 33.6, 29.4, 28.7, 26.6, 25.8. This amide (198 mg, 0.64 mmol) was dissolved in dichloromethane (4 mL) and trifluoroacetic acid (2 mL) was added and stirred for 2 h until all of the amide was consumed. The volatile substances were removed under vacuum. The residue was dissolved in ethyl acetate (50 mL), and washed with 5% $NaHCO_3$ (2×40 mL) and brine, dried (sodium sulfate), filtered and concentrated to give the amine 5 (132 mg, 98%). $^1$H NMR (400 MHz, $CDCl_3$) δ 6.76 (brs, 1H), 5.79 (m, 1H), 4.97 (m, 2H), 3.24 (m, 2H), 3.09 (s, 1H), 2.08 (m, 2H), 1.65 (brs, 2H), 1.56-1.40 (m, 4H), 1.00 (s, 9H); $^{13}$C NMR (100 MHz, $CDCl_3$) δ 173.3, 138.4, 114.8, 64.5, 38.8, 34.0, 33.3, 29.1, 26.7, 26.3. HRESI-MS: $C_{12}H_{24}N_2ONa^+$ ([M+Na]$^+$), calc'd 235.1781, found 235.1787.

$N^α$-{[(2R-N-Benzyloxy-N-formylamino)methyl]-6-heptenoyl}-N-(5-hexen-1-yl)-L-tert-leucinamide (3). This compound was prepared by coupling amine 5 and acid 4 in a manner similar to that of 9 (89% yield). $^1$H NMR (400 MHz, $CDCl_3$) δ 8.11 (brs, 0.6H), 7.85 (brs, 0.4H), 7.37 (m, 5H), 6.70 (brs, 1H), 6.60 (brs, 1H), 5.74 (m, 2H), 4.95 (m, 5H), 4.78 (brs, 1H), 4.32 (d, J=9.5 Hz, 1H), 3.75-3.68 (m, 1.6H), 3.30 (m, 1H), 3.08 (m, 1.4H), 2.65 (m, 1H), 2.07-1.97 (m, 4H), 1.53-1.35 (m, 8H), 0.96 (s, 9H); $^{13}$C NMR (100 MHz, $CDCl_3$) δ 173.3, 170.3, 162.8, 138.3, 138.0, 134.2, 129.6, 129.1, 128.7, 115.0, 114.8, 60.5, 46.1, 45.3, 44.9, 39.3, 34.4, 33.5, 33.3, 30.2, 29.0, 26.6, 26.2, 26.1.

N-(3-tert-Butyl-2,5-dioxo-1,4-diaza-cyclopentadec-10-en-6-ylmethyl)-N-benzyloxy-formamide (14). To a solution of diene 3 in dichloromethane (1.0 mM) was added 7% molar equivalent of Grubb's ruthenium catalyst.[35] The solution was stirred at 40° C. for ~20 h, allowed to cool to room temperature; and concentrated to dryness. The residue was purified by flash chromatography to give the cyclic monomer 14 (83% yield). $^1$H NMR (250 MHz, $CDCl_3$) δ 8.13 (brs, 0.6H), 7.90 (brs, 0.4H), 7.37 (m, 5H), 6.31 (m, 2H), 5.44-5.23 (m, 2H), 4.94 (m, 1H), 4.79 (brs, 1H), 4.18 (m, 1H), 3.76-3.59 (m, 3H), 3.10 (brs, 0.3H), 2.82 (m, 0.5H), 2.79-2.52 (m, 1.2H), 2.13-1.83 (m, 4H), 1.63-1.26 (m, 8H), 0.97 (s, 4.5H), 0.95 (s, 4.5H); $^{13}$C NMR (63 MHz, $CDCl_3$) δ 171.3, 131.5, 130.0, 129.6, 129.1, 61.3, 54.3, 45.7, 39.6, 38.9, 34.3, 34.1, 32.1, 31.8, 31.2, 29.7, 29.4, 28.5, 28.2, 27.4, 27.4, 27.1, 26.9, 26.8. HRESI-MS: $C_{26}H_{39}N_3O_4Na^+$ ([M+Na]$^+$), calc'd 480.2833, found 480.2875.

N-(3-tert-Butyl-2,5-dioxo-1,4-diaza-cyclopentadec-6-ylmethyl)-N-hydroxy-formamide (2). The cyclic compound 14 (50.0 mg) was dissolved in ethyl acetate and methanol (1:1, 10 mL) and 20 mg of 10% Pd/C as added. The mixture was exposed to 1 atm of hydrogen until all the starting material was consumed. The charcoal was removed by filtration and the filtrate was concentrated to give the desired compound quantitatively. $^1$H NMR (250 MHz, $CDCl_3$) δ 9.39 (brs, 1H), 8.37 (brs, 0.27H), 7.86 (brs, 0.73H), 7.40 (d, J=8.7 Hz, 0.27H), 6.94 (brs, 1H), 6.57 (brs, 0.73H), 4.33 (m, 1H), 3.81 (m, 2H), 3.43 (m, 1H), 2.87 (m, 2H), 1.64 (brs, 2H), 1.45-1.23 (m, 16H), 0.96 (s, 9H); $^{13}$C NMR (63 MHz, $CDCl_3$) δ 175.0, 173.3, 171.2, 170.9, 157.2, 61.1, 60.4, 52.7, 44.5, 38.5, 34.6, 29.8, 28.0, 27.8, 27.5, 26.8, 26.5, 25.2, 21.1, 14.2. HRESI-MS: $C_{19}H_{35}N_3O_4Na^+$ ([M+Na]$^+$), callc'd 392.2520, found 392.2504. HPLC analysis showed a purity of ~96% (FIG. 1).

EXAMPLES 1-5

Synthesis of Additional Antibiotic Compounds 1E-5E The following compounds were synthesized using the same method as disclosed for compound 2, above:

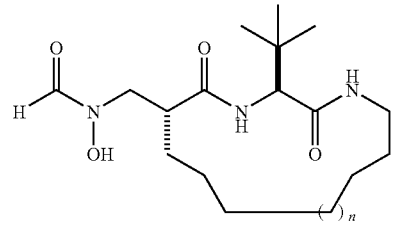

| Example No. | Compound No. | n |
|---|---|---|
| 1 | 1E | 1 |
| 2 | 2 | 3 |
| 3 | 3E* | 4 |
| 4 | 4E | 5 |
| 5 | 5E | 8 |

*Compound 2 of Example 2 is the same as compound 2, discussed above.

EXAMPLES 6-7

Synthesis of Antibiotic Compounds 6E and 7E The following compounds were synthesized using the same general methods.

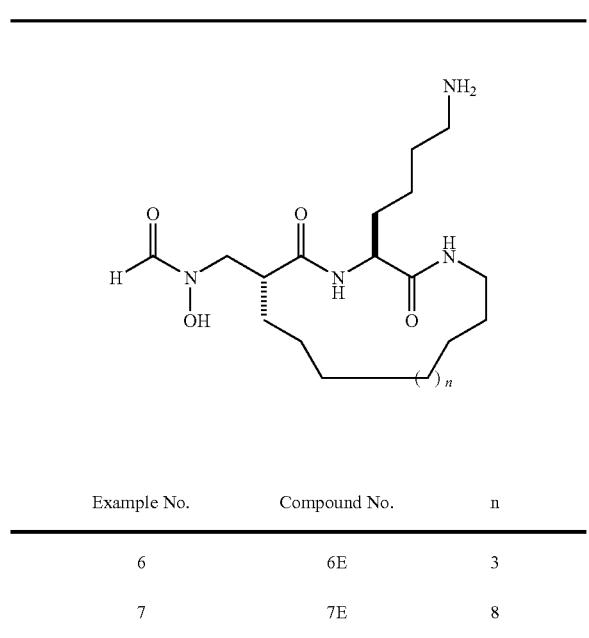

| Example No. | Compound No. | n |
|---|---|---|
| 6 | 6E | 3 |
| 7 | 7E | 8 |

EXAMPLE 8

Synthesis of Antibiotic Compounds 8E Compound 8E was synthesized using the same method as compound 2.

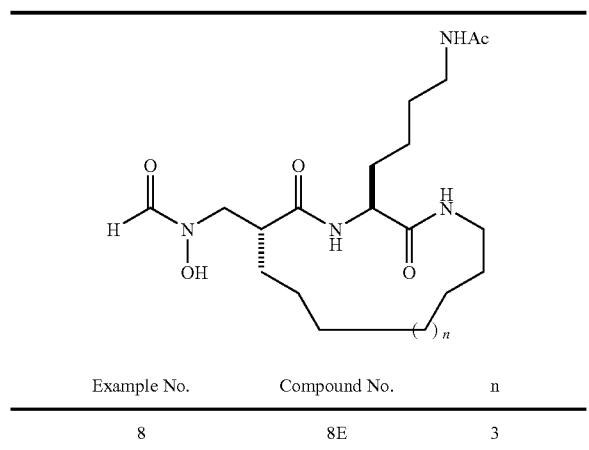

| Example No. | Compound No. | n |
|---|---|---|
| 8 | 8E | 3 |

COMPARATIVE EXAMPLES 9-10

Comparative compounds 9C and 10C were synthesized to compare to Compounds 1E-8E. BB-3497 was obtained from British Biotech for comparative purposes.

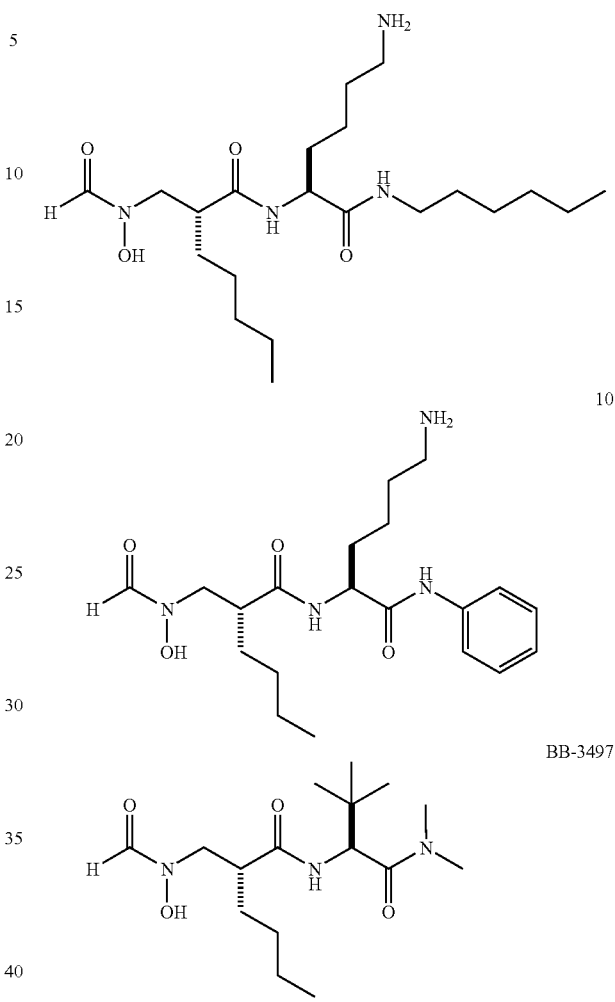

EXAMPLES 11-21

PDF Assays. The PDF reaction was coupled to formate dehydrogenase (FDH).[36] Assay reactions (total volume of 500 μL) typically contained 50 mM Mops (pH 7.0), 5 mM $NAD^+$, 0.5 unit FDH, 0-120 nM inhibitor 1 or 2, and 4 nM $E.$ $coli$ PDF. The mixture was reinsulated on ice for 1 h. The reaction was initiated by the addition of substrate formyl-Met-Leu-p-nitroaniline (final concentration of 200 μM) as the last component and the reaction progress was monitored continuously at 365 nm on a Perkin-Elmer Lambda-20 UV-Vis spectrophotometer. Due to the poor activity (high $K_M$ value) of FDH, the progress curves typically had an early lag phase (0-30 s) before finally reaching a linear phase (steady state). The initial rates were calculated from the linear region of the progress curves and fitted to the Michaelis-Menten equation $$V=(V_{max}*[S])/(K_M(1+[I]/K_I)+[S])$$

to obtain the apparent inhibition constant ($K_I$). An average $K_I$ value of 0.67±0.20 nM was obtained from multiple sets of data.

| Example | Compound | $K_1$ (nM) |
|---|---|---|
| 11 | 1E | 14 ± 3 |
| 12 | 2 | 0.67 ± 0.20 |
| 13 | 3E | 0.40 |
| 14 | 4E | 0.22 |
| 15 | 5E | 25 ± 6 |
| 16 | 6E | 3.0 ± 1.3 |
| 17 | 7E | 36 ± 9 |
| 18 | 8E | 12 ± 4 |
| 19 | 9C | — |

-continued

| Example | Compound | $K_1$ (nM) |
|---|---|---|
| 20 | 10C | 18 ± 1 |
| 21 | BB-3497 | ~7 |

EXAMPLE 22

Aminopeptidase Assay of Compound 2 The inhibition constant was also determined independently using and aminopeptidase assay.[37] Assay reactions (total volume of 500 µL) containing 50 mM Hepes (pH 7.0), 150 mM NaCl, 8.0 nM *E. coli* PDF, and 0-50 nM inhibitor 2 were incubated on ice for 2 h. Prior to reaction initiation, the mixture was brought to room temperature for 10 min. The PDF reaction was then initiated by the addition of substrate formyl-Met-Leu-p-nitronilide (final concentration 110 µM) and allowed to proceed for 3 min at room temperature before being quenched by heating at 95° C. for 10 min (the inactivation process is usually complete within the first 30 s). After cooling to room temperature, 1.0 unit of *Aeromonas* aminopeptidase (AAP) was added to the solution and the mixture was incubated for 15 min at room temperature. The absorbance at 405 nm was measured on a UV-Vis spectrophotometer. The initial rates were fitted to the above equation to obtain the $K_I$ value (0.33±0.15 nM). For all end-point assay reactions, the substrate to product conversion was kept at <20%.

Antimicrobial Susceptibility Testing. For *Escherichia coli* and *Bacillus subtilis*, cell growth was monitored on the Lambda-20 UV/Vis spectrophotometer at 600 nm. A single bacterial colony from a plate culture was grown overnight in LB media and was diluted 1000-fold into 2 mL of fresh growth medium containing 0-64 µg/mL of test agent in a 5-mL glass test tube shaken at a speed of 250 rpm. Cell growth (at 37° C.) was monitored for 0-600 min.

EXAMPLES 23-30

Inhibition of Metalloproteases (MMP) Several of the inhibitors were tested for inhibition of human matrix metalloproteases, which are often used as indicators of inhibitor selectivity (no inhibition of MMP is desired). Each inhibitor was tested at two different concentrations (1.0 and 10 µM). The values reported are the percentage of MMP activity remaining in the presence of added inhibitor.

| | | MMP-1 | | MMP2 | | MMP-3 | | MMP-9 | |
|---|---|---|---|---|---|---|---|---|---|
| Example | Inhibitor | 1.0 µM | 10 µM | 1.0 µM | 10 µM | 1.0 µM | 10 µM | 1.0 µM | 10 µM |
| 23 | 1E | 100 | 99 | 90 | 85 | 97 | 80 | 92 | 89 |
| 24 | 2 | 93 | 86 | 96 | 92 | 97 | 91 | 95 | 91 |
| 25 | 4E | — | — | — | — | — | — | — | — |
| 26 | 5E | 93 | 92 | 100 | 100 | 97 | 96 | 96 | 94 |
| 27 | 7E | 99 | 93 | 94 | 85 | 100 | 94 | 96 | 95 |
| 28 | 8E | 97 | 87 | 83 | 80 | 100 | 92 | 92 | 92 |
| 29 | 9C | 50 | 00 | 27 | 2 | 19 | 1 | 39 | 6 |
| 30 | 10C | 50 | 3 | 66 | 45 | 32 | 27 | 46 | 11 |

The cyclic compounds (1E-8E) show little inhibition of any of the MMPs, whereas the acyclic inhibitors (9C and 10C) showed substantial inhibition of all of the MMP's. The cyclic compounds are restricted to certain conformations, which are complementary to the PDF active site (by design) but do not fit the active sites of MMP's. The acyclic inhibitors are flexible and can adopt different conformations to fit the active sites of both PDF and MMP's.

EXAMPLES 31-35

Antibacterial Activity of PDF Inhibitors Inhibitors 2-7E were tested against two or more bacterial strains for antibacterial activities. The results are set forth below.

| | MIC (µg/mL) Example No./Compound No. | | | | |
|---|---|---|---|---|---|
| Bacteria | 31/2 | 32/4E | 33/5E | 34/6E | 35/7E |
| *E. coli* | ~12 | >24 | >24 | 4-8 | >32 |
| *B. subtilis* | 0.7-1.4 | ~0.2 | ~16 | ~8 | >32 |
| *E. faecalis* (ATCC 29212) | >32 | | >32 | | 32 |
| *H. influenzae* (ATCC 31517) | 0.5 | | >32 | | 32 |
| *M. catarrhalis* (ATCC 37054) | 0.62 | | <0.031 | | 1 |
| *S. aureus* (ATCC 29213) | 16 | | >32 | | 32 |
| *S. pneumoniae* (ATCC 49619) | 4 | | 8 | | >32 |
| *S. pneumoniae* (ATCC 6301) | 4 | | 8 | | >32 |
| *S. pneumoniae* (ATCC 6303) | 2 | | 4 | | >32 |

Molecular Modeling. The inhibitor was designed on the basis of the structure of *E. coli* PDF complexed with the N-formyl-hydroxylamine inhibitor 1 (PDB access code 1G27) with the modeling program FLO/QXP.[38] The binding site model consisted of all protein residues within 10.0 Å of inhibitor 1. In the binding site model the P1' n-butyl and P3' side chains of inhibitor 1 were crosslinked with poly(methylene) linkers of various lengths, followed by energy minimization with the peptide backbone fixed. Only the molecule with a nonyl group between the P1' Cα carbon and the P3' amino group (Compound 2) was able to fit in the binding site while maintaining staggered conformations in the linker. Subsequently, the entire molecule was subjected to torsional Monte Carlo docking searches, but no lower energy binding modes were found than the designed one.

Figure 7:
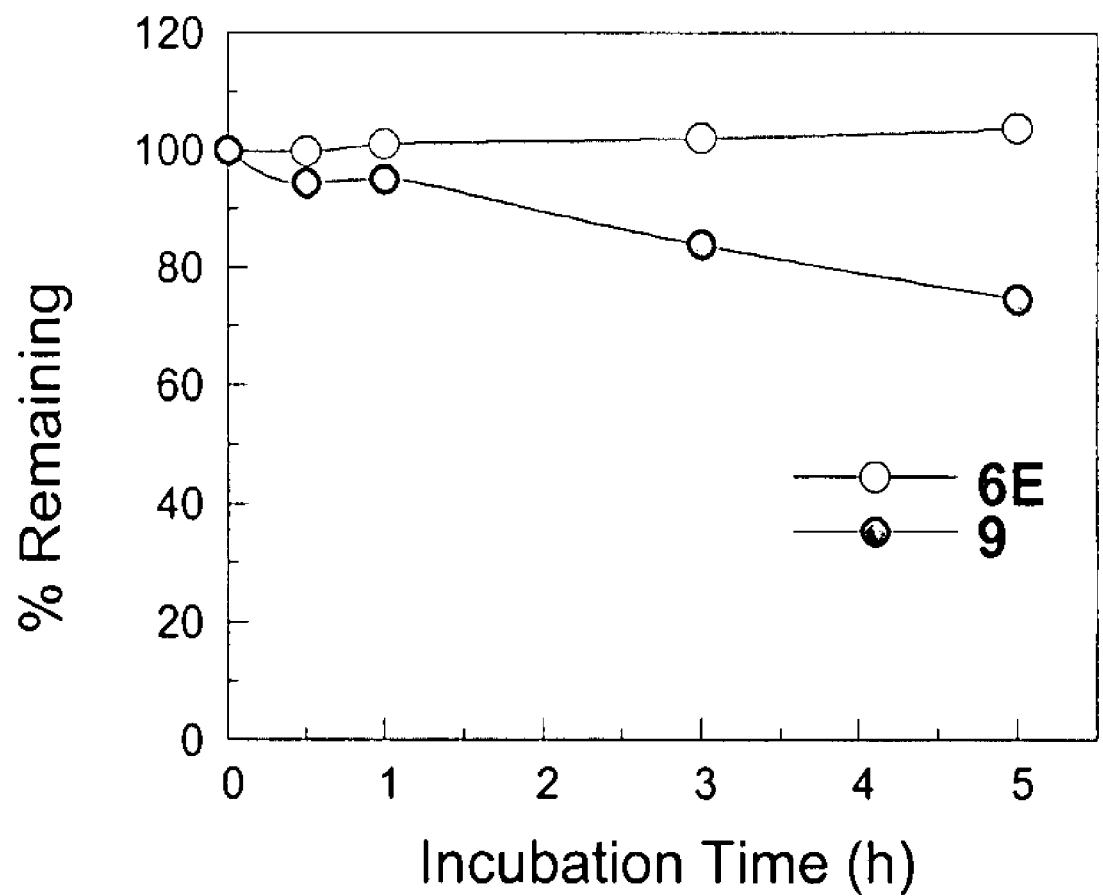
FIG. 7 Comparison of the in vitro stability of PDF inhibitors 6 (cyclic) and 9 (acyclic) in rat plasma.

Stability of Inhibitors Inhibitors 6E and comparative compound 9 were chosen to test for the effect of cyclization on inhibitor stability. They both have an L-lysine as the $P_2'$ residue and are expected to be sensitive to proteolytic degradation by trypsin-like enzymes. Both inhibitors were incubated in rat plasma at 37° C. and aliquots were withdrawn at various times and analyzed by LC-MS. The cyclic inhibitor (6E) was very stable under the experimental conditions, showing no detectable degradation after 5 h (FIG. 7). In contrast, the acyclic compound (9) showed time-dependent degradation, with approximately 25% loss after 5 h. Therefore, cyclization significantly improves the stability of the inhibitors against metabolic degradation. Our attempts to identify the degradation products by mass spectrometry failed.

All examples disclosed herein are for illustrative purposes only and are not meant to limit the claimed invention in any way.

REFERENCES

1. Giglione, C., Pierre, M., and Meinnel, T. Peptide deformylase as a target for new generation, broad spectrum antimicrobial agents. *Mol. Microbiol.* 2000, 36, 1197-1205.
2. Pei, D. Peptide deformylase: a target for novel antibiotics? *Emerging Therapeutic Targets* 2001, 5, 23-40.
3. Yuan, Z., Trias, J., and White, R. J. Deformylase as a novel antibacterial target. *Drug Discov. Today* 2001, 6, 954-961.
4. Meinnel, T., Mechulam, Y., and Blanquet, S. Methionine as translational start signal: a review of the enzymes of the pathway in *Escherichia coli. Biochimie* 1993, 75, 1061-1075.
5. Mazel, D., Pochet, S., and Marliere, P. Genetic characterization of polypeptide deformylase, a distinctive enzyme of eubacterial translation. *EMBO J.* 1994, 13, 914-923.
6. Meinnel, T., and Blanquet, S. Characterization of the *Thermus thermophilus* locus encoding peptide deformylase and methionyl-tRNA(fMet) formyltransferase. *J. Bacteriol.* 1994, 176, 7387-7390.
7. Margolis, P. S., Hackbarth, C. J., Young, D. C., Wang, W., Chen, D., Yuan, Z., White, R., and Trias, J. peptide deformylase in *S. aureus*: resistance to inhibition is mediated by mutations in the formyltransferase gene. *Antimicrob. Agents Chemother.* 2001, 44, 1825-1831.
8. Nguyen, K. T.; Hu, X.; Colton, C.; Chakratarti, R.; Zhu, M. X.; and Pei, D. Characterization of a human peptide deformylase: Implications for antibacterial drug design. *Biochemistry* (in press).
9. Rajagopalan, P. T. R., Yu, X. C., and Pei, D. Peptide deformylase: a new type of mononuclear iron protein. *J. Am. Chem. Soc.* 1997, 119, 12418-12419.
10. Groche, D., Becker, A., Schlichting, I., Kabasch, W., Schultz, S., and Wagner, A. F. V. Isolation and crystallization of functionally competent *Escherichia coli* peptide deformylase forms containing either iron or nickel in the active site. *Biochem. Biophys. Res. Commun.* 1998, 246, 342-346.
11. Rajagopalan, P. T. R., and Pei, D. Oxygen-mediated inactivation of peptide deformylase. *J. Biol. Chem.* 1998, 273, 22305-22310.
12. Meinnel, T., Patiny, L., Ragusa, S., and Blanquet, S. Design and synthesis of substrate analogue inhibitors of peptide deformylase. *Biochemistry* 1999, 38, 4287-4295.
13. Huntington, K. M., Yi, T., Wei, Y., and Pei, D. Synthesis and antibacterial activity of peptide deformylase inhibitors. *Biochemistry* 2000, 39, 4543-4551.
14. Wei, Y.; Yi, T.; Huntington, K. M.; Chaudhury, C.; and Pei, D. Identification of a potent peptide deformylase inhibitor from a rationally designed combinatorial library. *J. Comb. Chem.* 2000, 2, 650-657.
15. Chen, D. Z., Patel, D. V., Hackbarth, C. J., Wang, W., Dreyer, G., Young, D., Margolis, P. S., Wu, C., Ni, Z.-J., Trias, J., White, R., and Yuan, Z. Actinonin, a naturally occurring antibacterial agent, is a potent deformylase inhibitor. *Biochemistry* 2000, 39, 1256-1262.
16. Apfel, C., Banner, D. W., Bur, D., Dietz, M., Hirata, T., Hubschwerlen, C., Locher, H., Page, M. G. P., Pirson, W., Rosse, G., and Specklin, J.-L. Hydroxamic acid derivatives as potent peptide deformylase inhibitors and antibacterial agents. *J. Med. Chem.* 2000, 43, 2324-2331.
17. Jayasekera, M. M. K.; Kendall, A.; Sharmmas, R.; Dermyer, M.; Tomala, M.; Shapiro, M. A.; and Holler, T. P. Novel nonpeptidic inhibitors of peptide deformylase. *Arch. Biochem. Biophys.* 2000, 381, 313-316.
18. Thorarensen, A.; Douglas, M. R. Jr.; Rohrer, D. C. et al. Identification of novel potent hydroxamic acid inhibitors of peptidyl deformylase and the importance of the hydroxamic acid functionality on inhibition. *Bioorg. Med. Chem. Lett.* 2001, 11, 1355-1358.
19. Roblin, P. M.; and Hammerschlag, M. R. In vitro activity of a new antibiotic, NVP-PDF386 (VRC4887), against *Chlamydia pneumoniae. Antimicrob. Agents Chemother.* 2003, 47, 1447-1448.
20. Clements, J. M., Beckett, R. P., Brown, A., Catlin, G., Lobell, M., Palan, S., Thomas, W., Whittaker, M., Wood, S., Salama, S., Baker, P. J., Rodgers, H. F., Barynin, V., Rice, D. W., and Hunter, M. G. Antibiotic activity and characterization of BB-3497, a novel peptide deformylase inhibitor. *Antimicrob. Agents Chemother.* 2001, 45, 563-570.
21. Smith, H. K.; Beckett, R. P.; Clements, J. M.; Doel, S.; East, S. P.; Launchbury, S. B.; Pratt, L. M.; Spavold, Z. M.; Thomas, W.; Todd, R. S.; Whittaker, M. Structure-activity relationship of the peptide deformylase inhibitor BB-3497: modification of the metal binding group. *Bioorg. Med. Chem. Lett.* 2002, 12, 3595-3599.
22. Xue, C.-B.; He, X.; Roderick, J. et al. Design and synthesis of cyclic inhibitors of matrix metalloproteases and TNF-α production. *J. Med. Chem.* 1998, 41, 1745-1748.
23. Wei, C.-Q.; Gao, Y.; Lee, K. et al. Macrocyclization in the design of Grb2 SH2 domain-binding ligands exhibiting high potency in whole-cell systems. *J. Med. Chem.* 2003, 46, 244-254.
24. Hao, B., Gong, W., Rajagopalan, P. T. R., Zhou, Y., Pei, D., and Chan, M. K. Structural basis for the design of antibiotics targeting peptide deformylase. *Biochemistry* 1999, 38, 4712-4719.
25. Guilloteau, J-P., Mathieu, M., Giglione, C., Blanc, V., Dupuy, A., Chevrier, M., Gil, P., Famechon, A., Meinnel, T., and Mikol, V. The crystal structures of four peptide deformylases bound to the antibiotic actinonin reveal two distinct types: A platform for the structure-based design of antibacterial agents. *J. Mol. Biol.* 2002, 320, 951-962.

26. Evans, D. A.; Rieger, D. L.; Bilodeau, M. T.; Urpi, F. Stereoselective aldol reactions of chlorotitanium enolates. An efficient method for the assemblage of polypropionate-related synthons. *J. Am. Chem. Soc.* 1991; 113, 1047-1049.

27. Mitsunobu, O. The use of diethyl azodicarboxyalte and triphenylphosphane in synthesis and transformation of natural products. *Synthesis* 1981, 1-28.

28. Miller, S. J.; Blackwell, H. E.; Grubbs, R. H. Application of ringclosing metathesis to the synthesis of rigidified amino acids and peptides. *J. Am. Chem. Soc.* 1996, 118, 9606-9614.

29. Furstner, A. Olefin metathesis and beyond. *Angew. Chem., Int. Ed.* 2000, 39, 3012-3043.

30. Rajagopalan, P. T. R., Datta, A., and Pei, D. Purification, characterization, and inhibition of peptide deformylase from *Escherichia coli. Biochemistry* 1997, 36, 13910-13918.

31. Lazennec, C., and Meinnel, T. Formate dehydrogenase-coupled spectrophotometric assay of peptide deformylase. *Anal. Biochem.* 1997, 244, 180-182.

32. Bertinli, I.; Luchinat, C. The reaction pathways of zinc enzymes and related biological catalysts. In *Bioinorganic Chemistry*; Bertini, I., Gray, H. B., Lippard, S. J., Valentine, J. S., Eds.; University Science Books; California, 1994; pp 37-106.

33. Rajagopalan, P. T. R., Grimme, S., and Pei, D. Characterization of Cobalt(II)-Substituted Peptide Deformylase Function of the Metal Ion and the Catalytic Residue Glu-133. *Biochemistry* 2000, 39, 779-790.

34. Prescott, J. M.; Wilkes, S. H. *Aeromonas* aminopeptidase. *Methods Enzymol.* 1976, 45B, 530-543.

35. Miller, S. J.; Blackwell, H. E.; Grubbs, R. H. Application of ringclosing metathesis to the synthesis of rigidified amino acids and peptides. *J. Am. Chem. Soc.* 1996, 118, 9606-9614.

36. (a) Rajagopalan, P. T. R., Datta, A., and Pei, D. Purification, characterization, and inhibition of peptide deformylase from *Escherichia coli. Biochemistry* 1997, 36, 13910-13918. (b) Lazennec, C., and Meinnel, T. Formate dehydrogenase-coupled spectrophotometric assay of peptide deformylase. *Anal. Biochem.* 1997, 244, 180-182.

37. Wei, Y.; Pei, D. Continuous Spectrophotometric Assay of Peptide Deformylase. *Anal. Biochem.* 1997, 250, 29-34.

38. McMartin, C.; Bohacek R. J. QXP: powerful, rapid computer algorithms for structure-based drug design. *J Comput.-Aided Mol. Des.* 1997; 11, 333-344.

What is claimed is:

1. A method of inhibiting the growth of a bacterium comprising contacting the bacterium with an antibacterially effective amount of a compound selected from:

part of

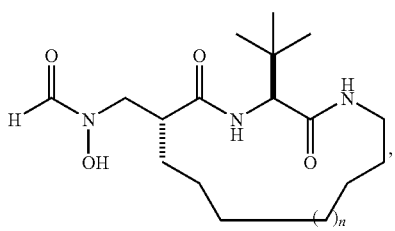

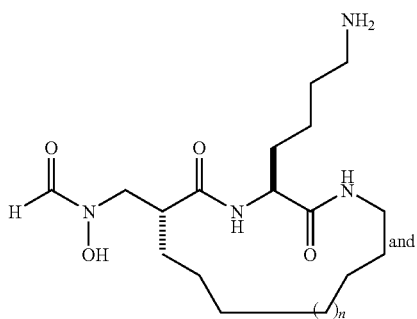

and

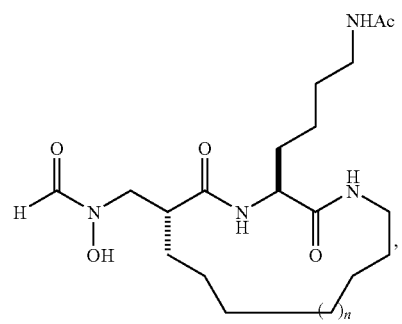

wherein n is 1 to 8.

2. The method of claim 1 wherein n is 3 to 5.

3. The method of claim 1, wherein the compound is

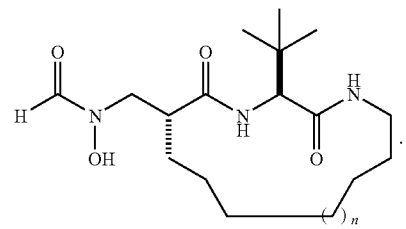

4. The method of claim 1, wherein the compound is

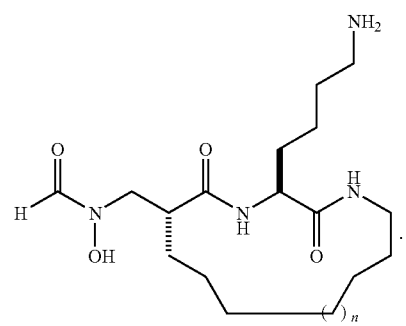

5. The method of claim 1, wherein the compound is

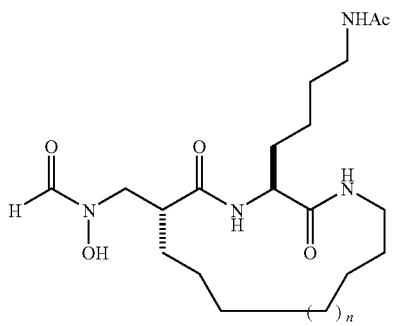

6. A method of treating a bacterial infection in a subject comprising administering to a subject in need thereof an effective amount of a compound selected from part of

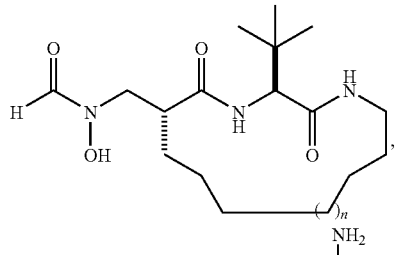

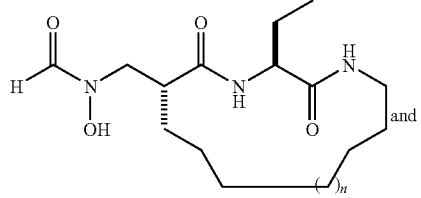

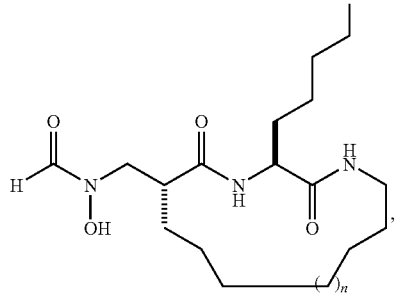

wherein n is 1 to 8.

7. The method of claim 6 wherein n is 3 to 5.

8. The method of claim 6, wherein the compound is

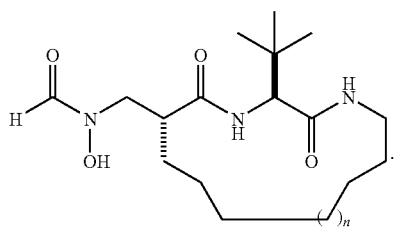

9. The method of claim 6, wherein the compound is

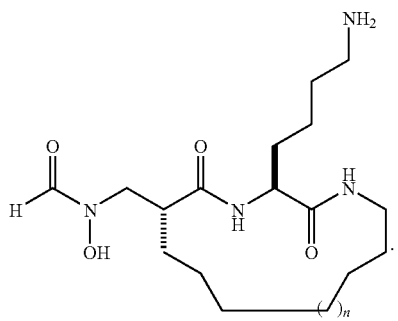

10. The method of claim 6, wherein the compound is

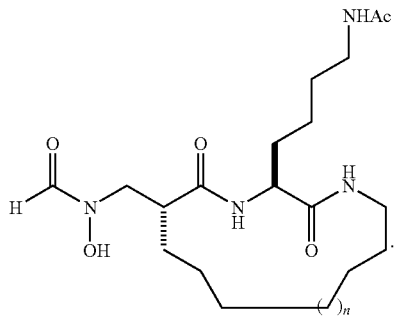

11. The method of claim 6 wherein the bacterial infection is a drug-sensitive bacterial infection.

12. The method of claim 6 wherein the bacterial infection is a drug-resistant bacterial infection.

13. The method of claim 6 wherein the subject is human.

* * * * *